United States Patent [19]
Hunt et al.

[11] Patent Number: 6,092,427
[45] Date of Patent: Jul. 25, 2000

[54] METHOD OF TESTING A BOND INTERFACE

[75] Inventors: Thomas J. Hunt, Peekskill; Paul S. Gilman, Suffern, both of N.Y.

[73] Assignee: Praxair S.T. Technology, Inc., North Haven, Conn.

[21] Appl. No.: 09/396,276

[22] Filed: Sep. 15, 1999

[51] Int. Cl.[7] .................................................. G01N 3/00
[52] U.S. Cl. ................................................. 73/835; 73/827
[58] Field of Search ........................... 73/826, 827, 828, 73/830, 834, 835, 838, 851

[56] References Cited

U.S. PATENT DOCUMENTS

| | | | |
|---|---|---|---|
| 3,538,757 | 11/1970 | Osborne | 73/835 |
| 4,027,529 | 6/1977 | Olsen | 73/827 |
| 4,550,613 | 11/1985 | Lehtikoski et al. | 73/834 |
| 5,181,424 | 1/1993 | Martin et al. | 73/835 |
| 5,673,586 | 10/1997 | Mann | 73/150 A |

*Primary Examiner*—Max Noori
*Attorney, Agent, or Firm*—Wood, Herron & Evans, L.L.P.

[57] ABSTRACT

A method of preparing and testing bond interface evaluation samples is provided for evaluating the strength of bonds between two metal components, such as the bond in a sputter target/backing plate assembly. A sample of the bond interface of the composite material is removed, a through hole is formed at one end, and the bond interface is removed in the area of the hole, thereby splitting the hole into two holes. The holes are grasped, such as by tapping the holes and inserting threaded rods therein, and the composite layers are pulled apart by applying oppositely directed forces to the rods. The strength of the bond, and not the component materials, is thereby evaluated.

28 Claims, 3 Drawing Sheets

METHOD OF TESTING A BOND INTERFACE

FIELD OF THE INVENTION

This invention relates to a method for testing the strength of a bond interface, and more specifically to a method of preparing and testing a sputter target/backing assembly evaluation sample to determine the strength of the bond between the sputter target and backing plate.

BACKGROUND OF THE INVENTION

Cathodic sputtering is widely used for the deposition of thin layers of material onto desired substrates. Basically, this process requires a gas ion bombardment of a sputter target having a face formed of a desired material that is to be deposited as a thin film or layer on a substrate. Ion bombardment of the target not only causes atoms or molecules of the target materials to be sputtered, but imparts considerable thermal energy to the target. This heat is dissipated beneath or around a backing plate that is positioned in a heat exchange relationship with the target. The sputter target forms a part of a cathode assembly that, together with an anode, is placed in an evacuated chamber filled with an inert gas, preferably argon. An electric field is applied across the cathode and the anode. The inert gas is ionized by collision with electrons ejected from the cathode. Positively charged gas ions are attracted to the cathode and, upon impingement with the target surface, these ions dislodge the target material. The dislodged target material traverses the evacuated enclosure and deposits as a thin film on the desired substrate, which is normally located close to the anode.

In a conventional target cathode assembly, the sputter target is attached at a single bonding surface to a nonmagnetic backing plate to form a parallel interface in the assembly. The backing plate provides a means for holding the target assembly in the sputtering chamber and provides structural stability to the target assembly. Also, the backing plate is normally water-cooled to carry away the heat generated by the ion bombardment of the target.

To achieve good thermal and electrical contact between the sputter target and the backing plate, these members are commonly attached to each other by use of soldering, brazing, diffusion bonding, solid state bonding, explosion bonding, mechanical fastening or epoxy bonding. The bond between the sputter target and the backing plate must accommodate stresses exerted on the target/backing plate assembly that occur upon cooling. If the bond is not sufficiently strong, the sputter target and backing plate will debond during service.

Quality assurance testing is performed by sputter target/backing plate assembly manufacturers and users to evaluate the strength of the bond interface to minimize occurrence of debonding during sputtering.

The current method for testing bond interfaces involves machining an evaluation sample to tight dimensions in which the thickness of the target layer is equal to the thickness of the backing plate layer, then clamping the sides of each of the component layers and subjecting the sample to a pull test. By this method, the evaluation samples are difficult to prepare due to the precise machining required, and the test results have proven unpredictable and unreliable. Often, the component materials, which are being squeezed by the clamps, yield before the bond interface is evaluated. There is uncertainty as to whether the results of the test apply to the strength of the bond interface or the strength of the materials comprising the sputter target and backing plate.

There is thus a need for a method of testing the strength of a bond interface in which the evaluation sample is simple to prepare and the results are repeatable and reliable.

SUMMARY OF THE INVENTION

The present invention provides a method for testing the strength of a bond between two metal components, specifically between a sputter target and backing plate. To this end, and in accordance with the principles of the present invention, an evaluation sample is prepared by machining out a sample from a sputter target/backing plate assembly and removing a portion of the bond interface, such as by saw cutting, at one end of the sample to form a slot that separates the sputter target from the backing plate By this method of the present invention, an evaluation sample is prepared having a non-bonded zone in which the sputter target material is separated from the backing plate material and a bonded zone in which the bond interface is maintained for testing. The sputter target component and backing plate component are then grasped in the non-bonded zone and pulled in opposite directions to break the bond in the bonded zone.

In a preferred embodiment of the present invention, a through hole is drilled in one end of the sample, and the slot is formed in that same end such that the hole is separated into two holes, one in the sputter target material and one in the backing plate material in the non-bonded zone, which holes may then be grasped and a steady force applied to pull apart the sputter target and backing plate components.

In an alternative method of the present invention, the portion of the bond interface may be first removed, followed by drilling one hole through the sputter target component to the slot or just partially into the component and drilling a second hole through the backing plate component to the slot or just partially into the component.

According to the principles of the present invention, the holes may be tapped with threads such that threaded rods may be inserted to grasp the holes, thereby facilitating the pull test. In the embodiments in which the holes are through holes, should the threads in one or both of these holes become stripped under the steady force, one or both of the rods may be secured by a nut and/or bolt within the slot separating the two metal components so that the pull test may be continued until failure.

Further to the principles of the present invention, the evaluation sample preferably has a length greater than the width, and the bonded zone is preferably longer than the non-bonded zone. Further, the holes are preferably substantially centered in the non-bonded zone.

There is thus provided a method for preparing and testing a sample of a sputter target/backing plate assembly or other metal composite that isolates the bond interface to easily and reliably evaluate the strength of the bond between the two metal components.

These and other objects and advantages of the present invention shall become more apparent from the accompanying drawings and description thereof.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the principles of the invention.

DETAILED DESCRIPTION

The present invention allows for the evaluation of the bond interface between two metal components by tensile testing or similar methods. The invention may apply to any metal composite material in which the layers of the composite are bonded together by soldering, brazing, diffusion bonding, solid state bonding, explosion bonding, mechanical fastening, epoxy bonding or other bonding method intended to create a strong interface between adjacent layers. One type of composite assembly of particular interest to the present inventors is the sputter target/backing plate assembly, which will be used hence forth to establish the principles of the present invention.

The principles of the present invention may be applied to a sputter target at any stage of use, from an unsputtered, bonded target blank to a target that has achieved full utilization. The metals or alloys comprising the composite components, i.e., the sputter target and backing plate, may be any metal or alloy, and the material for the sputter target may be similar or dissimilar to the material of the backing plate. The method of the present invention may be used on any configuration of sputter target/backing plate assembly and for any bonding method. The present invention allows for only the bond interface to be tested, while eliminating the error of mistakenly testing the strength of the composite materials.

Figure 1:
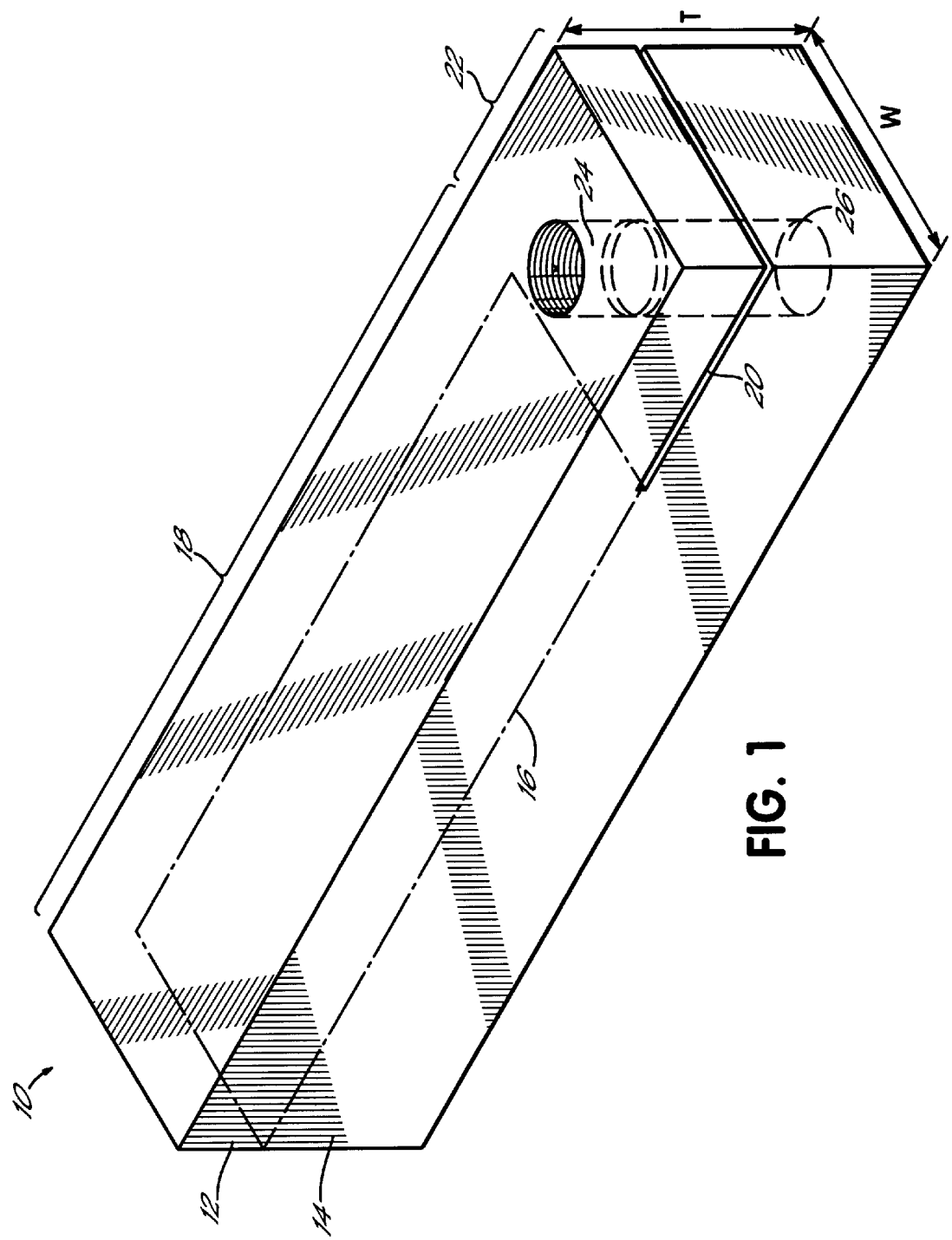
FIG. 1 is a perspective view of a bond interface evaluation sample of the present invention.

The present invention provides a method for preparing a sample of the bond interface of a sputter target/backing plate assembly (or other metal composite) and testing the sample, such as by tensile or pull testing, to determine the strength and reliability of the bond. To this end, and in accordance with the principles of the present invention, a test sample 10, as depicted in the perspective view of FIG. 1, is machined from a sputter target/backing plate assembly. The top metal component 12 comprises a portion from the sputter target (not shown), and the bottom metal component 14 comprises a portion from the backing plate (not shown). The two components 12,14 are joined at a bond interface 16 in a bonded zone 18 of the test sample 10, and are separated by a slot 20 in a non-bonded zone 22 of the test sample 10. The slot extends the entire width W of the sample, but preferably has a depth into the test sample such that the bonded zone 18 of test sample 10 is longer than the non-bonded zone 22. The thickness of the slot preferably substantially corresponds to or is greater than the thickness of the bond interface.

The thickness T of the test sample 10 and of the respective top and bottom components 12,14 is determined by the thickness of the sputter target/backing plate assembly (not shown), so there is no need for precise machining to establish tight dimensions with equal component thicknesses. The reliability of the testing method of the present invention is maximized when the bonded zone 18 is longer than the non-bonded zone 22, such as a length ratio of about 3:1. For ease of sample preparation, and for compatibility with most tensile testing apparatuses, the test sample preferably is machined to a width of about 0.5–1.5 inches and a length of 3–5 inches, with the bonded zone 18 having a length of 2.5–3.5 inches and the non-bonded zone 22 having a length of 0.5–1.5 inches.

The non-bonded zone 22 of test sample 10 has a hole 24 in the top component 12 and a hole 26 in the bottom component 14. Although the holes may be formed part way into each of the top and bottom components, it is preferred that the holes 24,26 be formed through to the slot 20. In a preferred embodiment of the present invention, the holes 24,26 are threaded to receive a threaded rod, bolt or other fastening device. The holes 24,26 are preferably substantially centered in the non-bonded zone 22 (also centered relative to the slot 20).

By way of example, and not limitation, a test sample of the present invention may have the following dimensions: 1.0 inch width; 4 inch total length; 1 inch×1 inch slot; ⅜ inch-16 thread through hole from top of titanium sputter target to bottom of aluminum backing plate, centered 0.5 inch from end and side of sample.

The slot 20 that separates the top component 12 (sputter target) from the bottom component 14 (backing plate) may be formed according to the principles of the present invention before or after the holes 24,26 are formed. If desired, a single hole may be drilled into one end of a fully bonded test sample, followed by forming a slot, such as by saw cutting, at the end containing the hole. The action of forming the slot 20 creates the non-bonded zone 22 by removing the bond interface 16 at one end of the sample and serves to separate the single hole into the two holes 24,26. Alternatively, the slot 20 may be formed first, and the two holes 24,26 formed simultaneously by drilling from the top through to the bottom, or vice versa, or formed separately by drilling into the top surface of the top component toward and preferably through to the slot 20 and by drilling into the bottom surface of the bottom component toward and preferably through to the slot 20. These embodiments allow for the sputter target material and the backing plate material to be separated in the region of the hole while maintaining a large region of bond interface in the adjacent portion of the sample for testing. Furthermore, these methods of preparing tensile or pull test samples is greatly simplified over prior methods of complex machining.

Once the test sample 10 of the present invention is machined, the holes are grasped and the top and bottom components 12,14 are pulled apart by a substantially steady force. To this end, and in accordance with the principles of the present invention, rods, bolts or other fastening members are secured in the holes 24,26. This is most easily accomplished by tapping the holes and screwing in threaded rods or bolts. Once the rods are attached, the test sample 10 is placed into a testing apparatus, such as any standard tensile test unit or any apparatus designed to simulate the loads applied by a standard tensile test apparatus. The rods are then grasped by the apparatus and the sputter target component is pulled in a direction away from the backing plate component, and the force needed to break the bond is measured. The backing plate component may remain stationary or may likewise be pulled in a direction away from the sputter target component. By this method, strain is applied to the bond interface 16 at the point where the bond interface 16 in the bonded zone 18 meets the slot 20 in the non-bonded zone 22, thereby testing the strength of the bond rather than the strength of the materials comprising the components 12,14.

While not shown, the components 12,14 may be pulled apart by a method other than forming holes in each component and attaching rods or other fastening members in the holes and pulling in opposite directions. The components 12,14, for example, could be clamped in the non-bonded zone 22 and the components 12,14 pulled apart. By way of further example, a threaded hole could be formed in the top component 12 and a threaded rod continuously screwed in through the slot 20 to the bottom component 14 until the bottom component 14 is pushed away from the top component 12 and the bond broken. In either example, by virtue of the slot 20, the strain will be concentrated at the bond interface 16 at the point where the bond interface 16 in the bonded zone 18 meets the slot 20 in the non-bonded zone 22, rather than within the materials comprising the components 12,14.

FIGS. 2–5 depict alternative methods of the present invention for testing the bond interface 16 between the two metal components 12,14, a sputter target and backing plate, respectively, of FIG. 1. In the method depicted in FIG. 2, threaded rods 28,30 are attached in holes 24,26, respectively, and the rods are grasped (not shown) by a tensile testing apparatus (not shown) and pulled in substantially opposite directions, as represented by the arrows. In the test portrayed in FIG. 2, the bond interface broke cleanly, representing a very weak bond.

Figure 3:
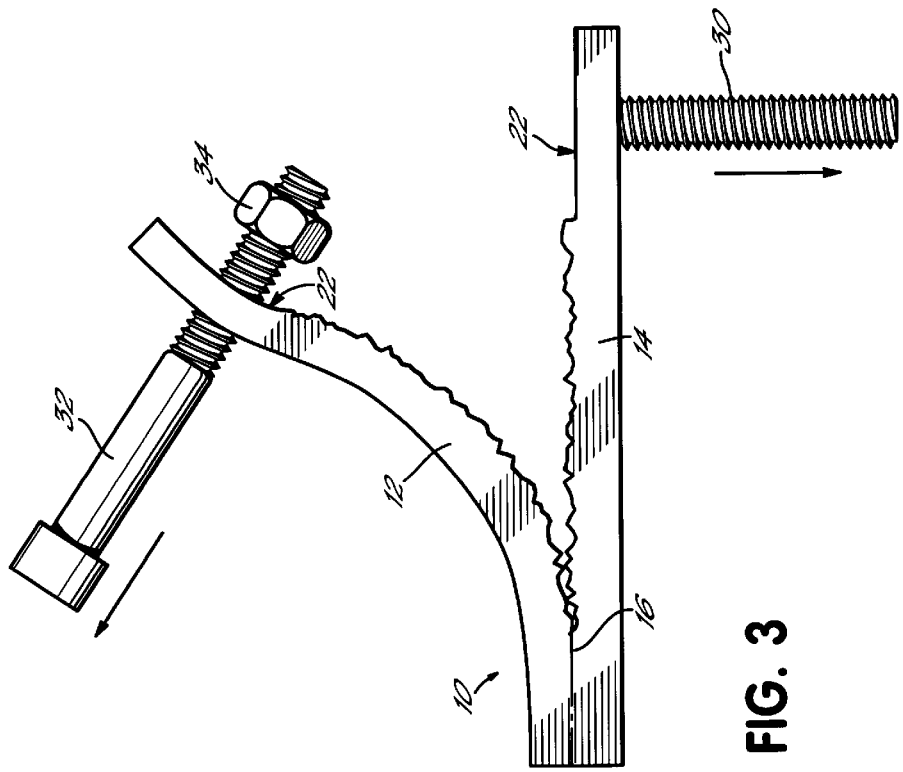
FIG. 3 is a sputter target/backing plate assembly evaluation sample tested by an alternative method of the present invention.
Figure 2:
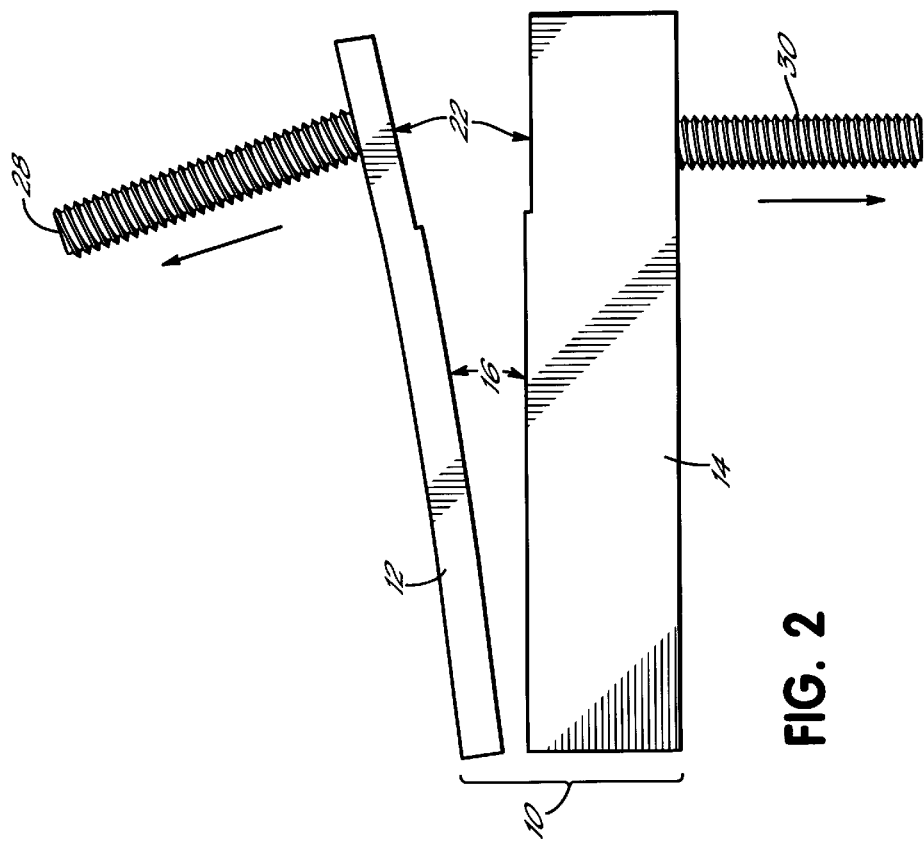
FIG. 2 is a sputter target/backing plate assembly evaluation sample tested by a method of the present invention.

In the method of the present invention depicted in FIG. 3, a threaded rod 30 is attached to hole 26 in the bottom component 14, while a threaded bolt 32 is attached to hole 24 in the top component 12. The two components 12,14 are pulled away from each other, resulting in a gradual tearing of the bond interface 16. The application of the steady force to the threaded holes, which puts strain on the bond interface, may also strip one or both of the holes 24,26, in particular, the top hole 24. Thus, part way into the pull test, when the slot has been opened up sufficiently, a nut 34 is secured within the opened slot to threaded bolt 32 to prevent the bolt from releasing its grasp of the hole 24 should the threads become stripped. In the test portrayed in FIG. 3, the bond interface tore gradually along the length of the sample, representing a weak-to-medium strength bond.

Figure 5:
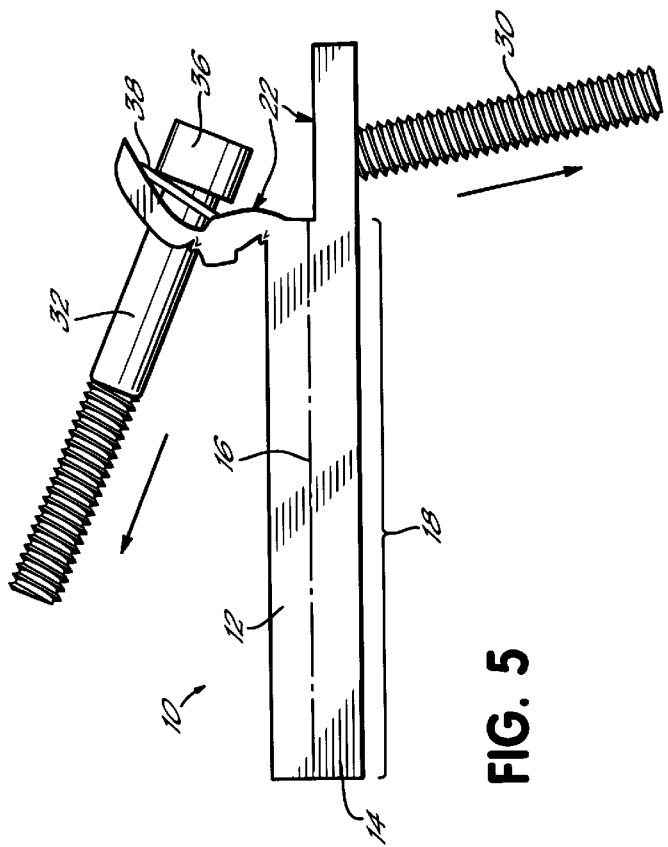
FIG. 5 is a sputter target/backing plate assembly evaluation sample tested by the method of FIG. 4 and depicting a strong bond interface.
Figure 4:
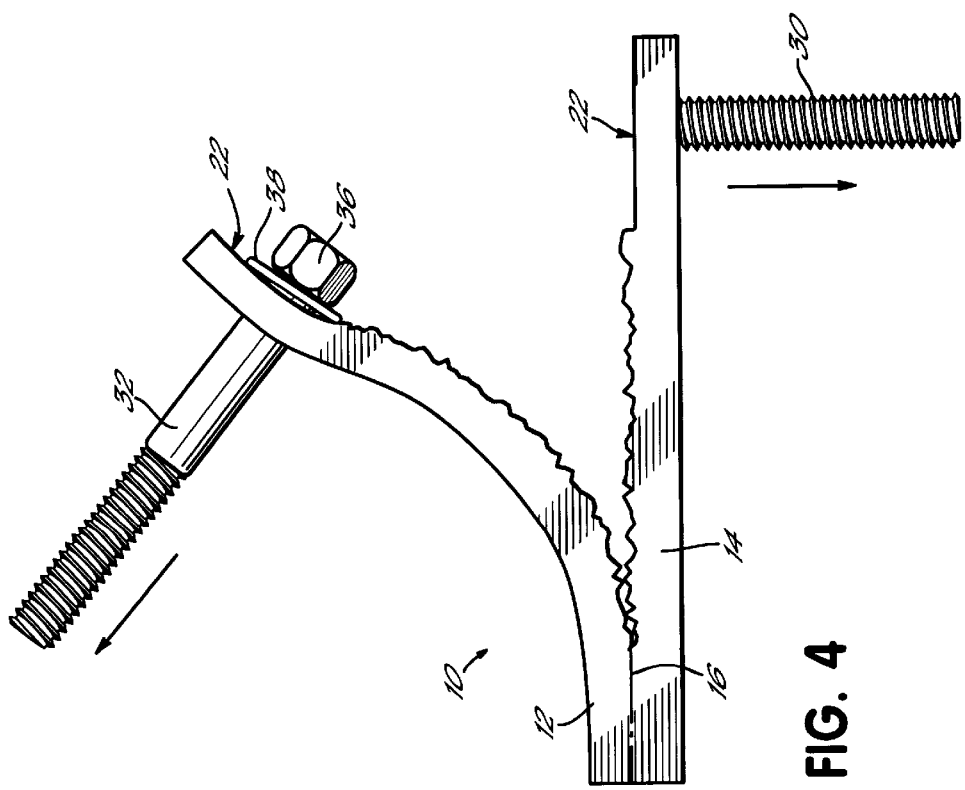
FIG. 4 is a sputter target/backing plate assembly evaluation sample tested by an alternative method of the present invention and depicting a weak bond interface.

In the method of the present invention depicted in FIGS. 4 and 5, a threaded rod 30 is attached to hole 26 in the bottom component 14, while a threaded bolt 32 is attached to hole 24 in the top component 12 such that the head 36 of the bolt 32 is within the slot. A washer 38 may also be used to protect the component materials from the bolt head 36. Due to the small thickness of the slot 20 before testing, the bolt 32 may be inserted in this fashion after first pulling to open up the slot by grasping the first hole with another method, such as a threaded rod screwed into the hole. This embodiment is useful were the threads have been stripped and the threads are no longer present to permit the rod to grasp the hole. In the test portrayed in FIG. 4, the bond interface tore gradually along the length of the sample, representing a weak-to-medium strength bond, just as with FIG. 3. In the test portrayed in FIG. 5, the bond interface was so strong that the two components did not separate in the bonded zone, and the material of the top component 12 deformed and tore in the non-bonded zone.

In use, the method of the present invention may be used to test composite materials before or after partial or full use to determine the reliability and strength of the bond interface between the two bonded layers. The method of the present invention provides a simple, consistent way to prepare and test bond interface evaluation samples, such as samples of sputter target/backing plate assemblies, wherein the results are reliable and reproducible.

While the present invention has been illustrated by the description of embodiments thereof, and while the embodiments have been described in considerable detail, they are not intended to restrict or in any way limit the scope of the appended claims to such detail. Additional advantages and modifications will readily appear to those skilled in the art. For example, while bonded sputter target/backing plate assemblies have been specifically identified, the present invention may be used to test the strength of the bond between any two layers of any metallic composite. Furthermore, while specific methods have been described for forming the slot and holes in the test sample, and for grasping the holes, it should be appreciated that other techniques and methods known to one skilled in the art may likewise be used in accordance with the principles of the present invention to achieve a reliable evaluation of the bond interface. The invention in its broader aspects is therefore not limited to the specific details, representative apparatus and method and illustrative examples shown and described. Accordingly, departures may be made from such details without departing from the scope or spirit of applicant's general inventive concept.

What is claimed is:

1. A method of testing the strength of the bond between the layers of a composite comprising a first metal component and a second metal component, where a surface of the first metal component is bonded to a surface of the second metal component to form a bond interface, the method comprising the steps of:

removing a volume of material comprising the bond interface from an end of the composite to form a slot that separates the first metal component from the second metal component to establish a non-bonded section at said end;

grasping the first metal component in the non-bonded section;

grasping the second metal component in the non-bonded section; and applying a force to the grasped first and second metal components that pulls the first metal component in a direction away from the second metal component until failure of the bond and measuring the force at failure.

2. The method of claim 1, further comprising forming a first hole in the first metal component in the non-bonded section and a second hole in the second metal component in the non-bonded section, wherein the steps of grasping the first and second metal components include engaging each of the first and second holes with a fastening member, and wherein the force application step includes the step of applying a force to the fastening members.

3. The method of claim 1, wherein the steps of grasping the first and second metal components include clamping each of the components in the non-bonded section.

4. A method of testing the strength of the bond between the layers of a composite comprising a first metal component and a second metal component, the composite having a bonded section where a surface of the first metal component is bonded to a surface of the second metal component and a non-bonded section where the surface of the first metal component is separated by a slot from the surface of the second metal component, the method comprising the steps of:

forming a first hole at least through a portion of the first metal component in the non-bonded section and forming a second hole at least through a portion of the second metal component in the non-bonded section;

grasping the first hole;

grasping the second hole; and applying a force to the grasped first and second holes that pulls the first metal component in a direction away from the second metal component until failure of the bond and measuring the force at failure.

5. The method of claim 4, further comprising tapping the first hole and screwing a threaded rod into the first hole to thereby grasp it, and wherein the force application step includes the step of applying a force to the threaded rod in a direction away from the second hole.

6. The method of claim 5, further comprising re-grasping the first hole by securing the rod within the slot after the threads in the first hole have been stripped by applying the force.

7. The method of claim 4, further comprising tapping the second hole and screwing a threaded rod into the second hole to thereby grasp it, and wherein the force application step includes the step of applying a force to the threaded rod in a direction away from the first hole.

8. The method of claim 4, wherein the nonbonded sections of the first and second components are grasped by engaging first and second bolts in the first and second holes, respectively.

9. The method of claim 4, further comprising forming the non-bonded section by removing a volume of material from the composite comprising a bond interface between the first and second metal components to form a slot therebetween, establishing the nonbonded section.

10. The method of claim 4, wherein the first and second holes are formed by first forming a single hole through the first and second metal components and then forming the non-bonded section by removing a volume of material from the composite comprising a bond interface between the first and second metal components to form a slot therebetween, establishing the non-bonded section, thereby separating the single hole into the first and second holes.

11. The method of claim 4, wherein the bonded section has a length greater than the length of the non-bonded section.

12. The method of claim 11, wherein the ratio of the length of the bonded section to the length of the non-bonded section is about 3:1.

13. The method of claim 4, wherein the composite has a width of about 0.5–1.5 inches, the bonded section has a length of about 2.5–3.5 inches, and the non-bonded section has a length of about 0.5–1.5 inches.

14. The method of claim 13, wherein the first and second holes are substantially centered in the non-bonded section.

15. The method of claim 4, wherein the composite is at least a portion of a sputter target/backing plate assembly, and the first metal component comprises at least a portion of a sputter target and the second metal component comprises at least a portion of a backing plate.

16. The method of claim 15, wherein the thickness of the composite is equal to the thickness of the sputter target/backing plate assembly.

17. A method of evaluating the strength of the bond between a sputter target and backing plate, comprising the steps of:

preparing a bond interface evaluation sample by machining out a sample from a sputter target/backing plate assembly, drilling a hole at a first end of the sample through the thickness of the sample, and removing a portion of the bond interface across the width of the sample at the first end to form a slot separating the sputter target from the backing plate and thereby dividing the hole into a top hole and a bottom hole;

attaching a first rod in the top hole and a second rod in the bottom hole; and engaging the first and second rods and applying a force thereto that pulls the sputter target and backing plate away from each other until failure of the bond and measuring the force at failure.

18. The method of claim 17, wherein the length of the sample is about 3.0–5.0 inches and the width is about 0.5–1.5 inches.

19. The method of claim 17, wherein the slot is formed to a length of about 0.5–1.5 inches.

20. The method of claim 17, wherein the top and bottom holes are substantially centered relative to the slot.

21. The method of claim 17, further comprising tapping the hole, wherein the first and second rods are threaded and are attached by screwing into the top and bottom holes.

22. The method of claim 21, further comprising securing the first rod within the slot after the threads in the top hole are stripped.

23. The method of claim 17, wherein the portion of the bond interface is removed by saw cutting.

24. A method of testing the strength of the bond between the layers of a composite comprising a first metal component and a second metal component, the composite having a bonded section where a surface of the first metal component is bonded to a surface of the second metal component and a non-bonded section where the surface of the first metal component is separated by a slot from the surface of the second metal component, the method comprising the steps of:

forming a first hole through the first metal component in the non-bonded section;

applying a force through the first hole that pushes the second metal component in a direction away from the first metal component until failure of the bond and measuring the force at failure.

25. A bond interface evaluation sample for testing the strength of the bond between a sputter target and a backing plate, comprising:

a sputter target component and a backing plate component;

a bonded zone where a surface of the sputter target component is bonded to a surface of the backing plate component to form a bond interface;

a non-bonded zone where the surface of the sputter target component is separated by a slot from the surface of the backing plate component;

a first hole in the non-bonded zone extending through the sputter target component; and a second hole in the non-bonded zone extending through the backing plate component, the first and second holes each adapted to receive a rod that upon application of force thereto in opposite directions are capable of pulling the sputter target component and the backing plate component in opposite directions to separate the sputter target and backing plate components from each other at the bonded interface.

26. The sample of claim 25, wherein the length of the bonded zone is about 2.5–3.5 inches, the length of the non-bonded zone is about 0.5–1.5 inches, the width of the sample is about 0.5–1.5 inches, and the first and second holes are substantially centered in the non-bonded zone.

27. The sample of claim 25, wherein the length of the bonded zone is about 3.0 inches, the length of the non-bonded zone is about 1.0 inches, the width of the sample is about 1.0 inches, and the first and second holes are substantially centered in the non-bonded zone.

28. The sample of claim 25, wherein the first and second holes are tapped for receiving threaded rods.

\* \* \* \* \*